United States Patent [19]
Komi

[11] Patent Number: 5,343,853
[45] Date of Patent: Sep. 6, 1994

[54] SIDE-LOOKING TYPE ELECTRONIC ENDOSCOPE WHICH ALLOWS MANIPULATING TOOL TO BE INSERTED THEREINTO

[75] Inventor: Shuji Komi, Omiya, Japan

[73] Assignee: Fuji Photo Optical Co., Ltd., Saitama, Japan

[21] Appl. No.: 934,260

[22] Filed: Aug. 25, 1992

[30] Foreign Application Priority Data

| | | |
|---|---|---|
| Sep. 20, 1991 [JP] | Japan | 3-084849[U] |
| Sep. 20, 1991 [JP] | Japan | 3-270222 |
| Sep. 20, 1991 [JP] | Japan | 3-270223 |

[51] Int. Cl.$^5$ ............................................. A61B 1/00
[52] U.S. Cl. ............................................. 128/4; 128/6
[58] Field of Search ............................................. 128/4, 6

[56] References Cited

U.S. PATENT DOCUMENTS

| | | | |
|---|---|---|---|
| 3,896,793 | 7/1975 | Mitsui et al. | 128/6 |
| 4,407,273 | 10/1983 | Ouchi | 128/6 |
| 4,452,236 | 6/1984 | Utsugi | 128/4 |
| 4,593,680 | 6/1986 | Kubokawa | 128/4 |
| 4,697,576 | 10/1987 | Krauter | 128/4 |
| 4,706,655 | 11/1987 | Krauter | 128/4 |
| 4,841,949 | 6/1989 | Shimizu et al. | 128/4 |
| 4,949,706 | 8/1990 | Thon | 128/4 |

Primary Examiner—Richard J. Apley
Assistant Examiner—Karen A. Jalbert
Attorney, Agent, or Firm—Ronald R. Snider

[57] ABSTRACT

A side-looking type endoscope which leads out a manipulating tool from the side surface of the end portion thereof. A raising table for raising a manipulating tool is provided at the end portion. An arcuate groove is formed in the raising table in such a manner that the arcuate groove has a linear bottom line and the inclination of the linear bottom line when the raising table is erect is different from the inclination of the wall of the exit passage of the manipulation tool insertion channel. An arcuate groove having a curvature radius suitable for guiding the manipulating tool which is bent when the raising table is erect is formed at a part of the arcuate groove having a linear bottom line, thereby enabling a smooth movement of the manipulating tool. If the exit passage of the manipulating tool insertion channel has an oval section having the major axis in the vertical direction, or the solid-state image sensor is disposed such that the surface of the device is perpendicular to the exit end surface of the endoscope, and the exit passage of the manipulating tool insertion channel is curved in a plane approximately parallel to the surface of device of the solid-state image sensor, it is easy to bend the manipulating tool at an even larger angle and with an even larger curvature radius.

6 Claims, 6 Drawing Sheets

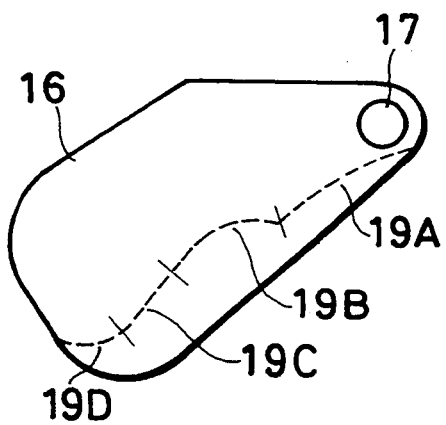
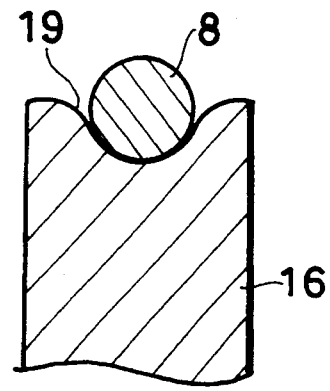
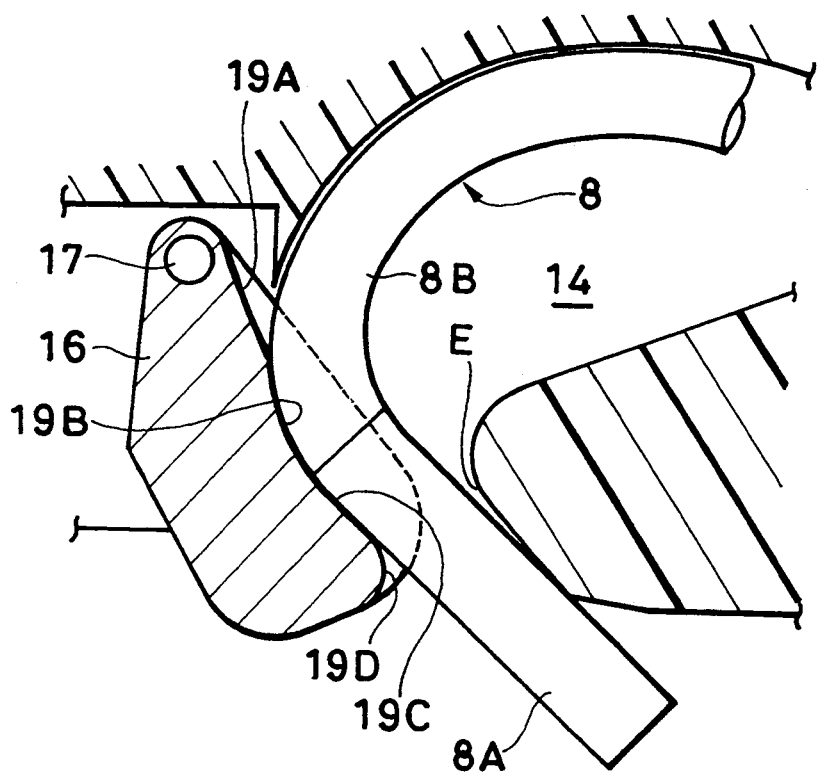

SIDE-LOOKING TYPE ELECTRONIC ENDOSCOPE WHICH ALLOWS MANIPULATING TOOL TO BE INSERTED THEREINTO

This application claims the priority of Japanese Patent Application Nos. 3-270222, 3-270223 and 3-84849 (UM) filed on Sep. 20, 1991, which are incorporated herein by reference.

BACKGROUND OF THE INVENTION

1. Field of the Invention

The present invention relates to a side-looking type endoscope which allows a manipulating tool to be inserted thereinto and, more particularly, to the structure of a side-looking type endoscope which leads a manipulating tool from the end portion toward the side surface of the endoscope.

2. Description of the Related Art

Electronic endoscopes having a charge coupled device (CCD), which is a solid-state image sensor, at the end portion and endoscopes for observing an image only by an optical means are conventionally known. Such an endoscope is not only used to observe the internal state of the body as the object of inspection but also used together with a manipulating tool such as forceps for the purpose of incision, biopsy and collection.

FIG. 11 shows the structure of the end portion of a conventional side-looking type electronic endoscope. In the side-looking type electronic endoscope, a forceps insertion hole 3 which communicates with the manipulating tool insertion channel 2, namely, a part of a manipulating tool insertion channel 2, an observation window (not shown), an irradiation window (not shown), etc. are provided not on the front surface but on the side surface of the end portion 1 of the endoscope. A CCD 4, which is a solid-state image sensor, is provided slightly above the middle portion in the endoscope. The CCD 4 picks up the image which is observed through the observation window. Through the side-looking type endoscope, it is therefore possible to observe and treat a diseased part which lies in the orthogonal direction relative to the direction of insertion of a manipulating tool.

A raising table 5 which rotates toward the forceps insertion hole 3 is attached to the side surface (at the lower portion) of the end portion 1 of the endoscope, and a wire 7 is connected to the raising table 5. The wire is also connected to an operating portion. By pulling the wire 7, the raising table 5 is rotated, thereby raising a manipulating tool 8, which is led out through the forceps insertion hole 3, up to a predetermined position, as indicated by the broken line. In this case, an arcuate groove 9 for guiding the manipulating tool 8 is formed in the raising table 5 so as to ensure the operation of bending the manipulating tool 8. Examples of the manipulating tool 8 are biopsy forceps, sterilizing forceps, high-frequency knife, high-frequency snare, high-frequency hemostatic tool, cytodiagnostic brush and injection needle. Various treatments are carried out while bending these manipulating tools 8.

A conventional endoscope, however, suffers from a problem that the smooth movement of the manipulating tool 8 is difficult in the state of being bent by the raising table 5. More specifically, the arcuate groove 9 formed in the raising table 5 in such a manner as to be engaged with the manipulating tool 8 has a gently curved bottom line, as shown in FIG. 12, so that, in the state in which the raising table 5 is erect, the raising table 5 comes into contact with the manipulating tool 8 at a point A of the arcuate groove 9. At this time, since the manipulating tool 8 is bent at a large angle, the force applied to the manipulating tool 8 for moving the manipulating tool 8 does not act effectively thereon, thereby making a smooth movement of the manipulating tool 8 impossible. Recently, the angle at which the manipulating tool 8 is bent has a tendency of being increased, and a measure for enabling a smooth movement of the manipulating tool 8 is demanded.

In a conventional endoscope, it is impossible to bend the manipulating tool 8 at the forceps insertion hole 3, which is the exit passage of the manipulating tool insertion channel 2, at a large angle. Since the manipulating tool insertion channel 2 is composed of a circular pipe, the section of the forceps insertion hole 3 at the exit passage of the manipulating tool insertion channel is also circular (round). In addition, since the forceps insertion hole 3 is provided obliquely in a straight line, it is difficult to bend the manipulating tool 8 at a large angle.

It is further desired that the curvature radius of the curve formed by bending the manipulating tool 8 should be large. It is because if the curvature radius of the curve is small, the load applied to the manipulating tool 8 in the erect state becomes large, which prevents the functional operation of the manipulating tool 8 and shortens its life.

The curvature radius of the manipulating tool 8 and the angle at which the manipulating tool 8 is bent are not large in a conventional endoscope partly because it is impossible to incline the passage of the forceps insertion hole 3 at a large angle due to the presence of the CCD 4, so that the inclination of the forceps insertion hole 3 is gentle. As shown in FIG. 13, an observation window 52 is attached to the CCD 4 through an optical lens 51. The observation window 52 must be close to the forceps insertion hole 3 because the diseased part is treated while it is being observed. Therefore, the inclination of the forceps insertion hole 3 is determined with due consideration for the position of the CCD 4. In a conventional endoscope, however, the CCD 4 is disposed in the upper region of the endoscope which is the region where the manipulating tool insertion channel 2 is extended, as shown in FIG. 11, so that the presence of the CCD 4 limits the inclination of the forceps insertion hole 3, thereby making it impossible to allow the manipulation tool 8 to have a large curvature radius and to be bent at a large angle.

SUMMARY OF THE INVENTION

Accordingly, it is a first object of the present invention to eliminate the above-described problems in the related art and to provide a side-looking type endoscope which enables a smooth movement of a manipulating tool in the state in which a raising table is erect.

It is a second object of the present invention to provide a side-looking type endoscope which allows a manipulation tool to have a large curvature radius and to be bent at a large angle.

To achieve this end, a side-looking type endoscope provided in a first aspect of the present invention comprises:

a manipulation tool insertion channel provided in the endoscope; and a raising table disposed in the vicinity of the exit of the manipulation tool insertion channel so as to bend a manipulation tool toward the side surface of the endoscope in the state of being engaged with an arcuate groove which is formed in the raising table in such a manner that the arcuate groove has a linear bottom line and the inclination of the linear bottom line when the raising table is erect is different from the inclination of the wall of the exit passage of the manipulation tool insertion channel which faces the arcuate groove. According to this endoscope, when the raising table is erect, the manipulating tool comes into contact with the linear bottom line of the arcuate groove, and the linear bottom line serves as a guide for the manipulating tool without concentrating the force applied to the manipulating tool only on one point. Thus, a smooth movement of the manipulating tool is enabled. On the other hand, when the manipulating tool is led out through the exit, the manipulating tool is moved along the wall of the exit passage in close contact therewith, so that contact resistance which obstructs the smooth movement of the manipulating tool is not caused between the manipulating tool and the wall of the exit passage.

In a side-looking type endoscope provided in a second aspect of the present invention, an arcuate groove having a radius of curvature suitable for guiding the manipulating tool which is bent when the raising table erect is formed at a part of the arcuate groove formed on the raising table. An arcuate groove having a predetermined radius of curvature is formed at, for example, an intermediate portion of the raising table, and the bent portion of the manipulating tool comes into contact with the arcuate portion of the arcuate groove. Therefore, the arcuate portion serves as a guide for the bent manipulating tool, thereby facilitating the movement of the manipulating tool when the raising table is erect.

In a side-looking type endoscope provided in a third aspect of the present invention, the exit passage of the manipulating tool insertion channel at which the manipulating tool bent by the raising table is situated is so designed as to have an oval section with the major axis in the direction in which the manipulating tool is bent. According to this endoscope, the diameter of the exit passage is made larger in a plane at which the manipulating tool is bent than in a conventional endoscope, so that it is possible to bend the manipulating tool at a larger curvature and a larger angle than in a conventional endoscope. It is also possible to provide a curved wall as the upper wall of the exit passage.

In a side-looking type endoscope provided in a fourth aspect of the present invention, a solid-state image sensor is disposed at the end portion of the endoscope such that the surface of the device is perpendicular relative to the exit end surface of the endoscope, and the exit passage of the manipulating tool insertion channel is curved in the direction approximately parallel to the surface of the solid-state image sensor. According to this endoscope, since the solid-state image sensor is disposed such that the surface of the device is perpendicular relative to the exit end surface of the endoscope, it is possible to pass the manipulating tool insertion channel through the endoscope while keeping clear of the solid-state image sensor, thereby enabling the exit passage to be curved at a large angle. It is therefore possible to bend the manipulating tool which is inserted into the exit passage also at a large angle.

An appropriate combination of the above-described structures is usable so as to be applied to an endoscope and electronic endoscope using an optical means.

The above and other objects, features and advantages of the present invention will become clear from the following description of the preferred embodiments thereof, taken in conjunction with the accompanying drawings.

BRIEF DESCRIPTION OF THE DRAWINGS

FIG. 4 is an elevational view of the structure of the raising table of the first embodiment;

FIG. 5 is a sectional view of the side surface of the raising table shown in FIG. 4;

FIG. 6 is a sectional view of the first embodiment in the state in which the manipulating tool is bent by the raising table;

DESCRIPTION OF THE PREFERRED EMBODIMENTS

First Embodiment

Figure 1:
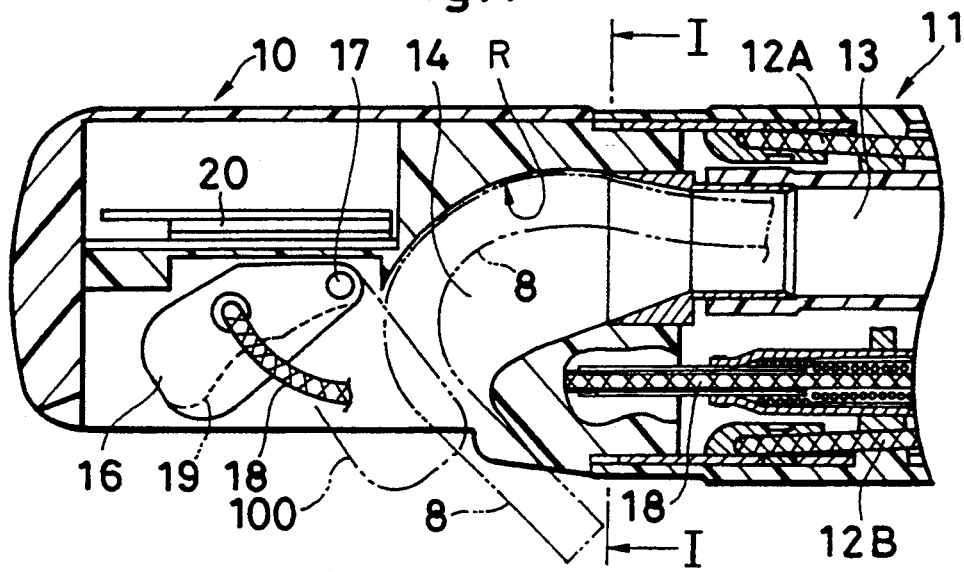
FIG. 1 is a sectional view of the structure of the side surface of the end portion of a first embodiment of a side-looking type endoscope which allows a manipulating tool to be inserted thereinto according to the present invention.
Figure 2:
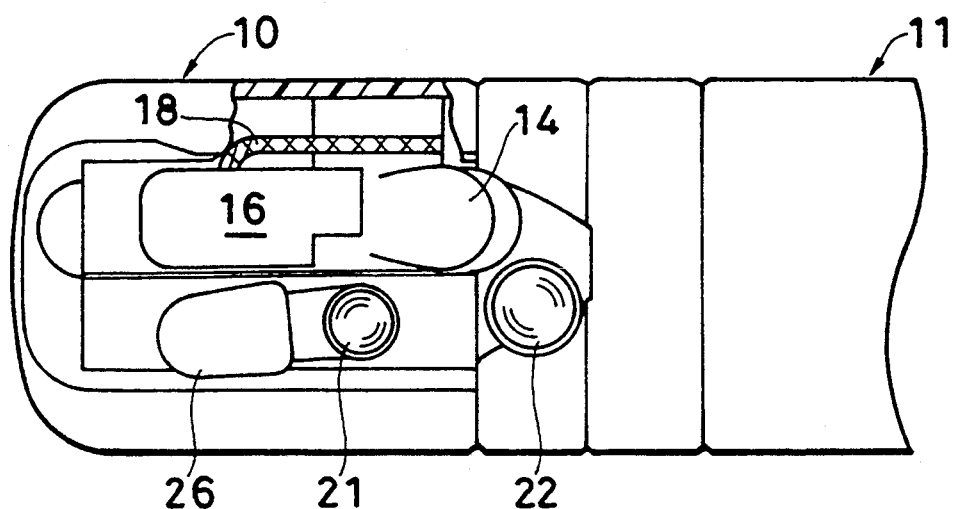
FIG. 2 is a bottom view of the end portion of the first embodiment shown in FIG. 1.
Figure 3:
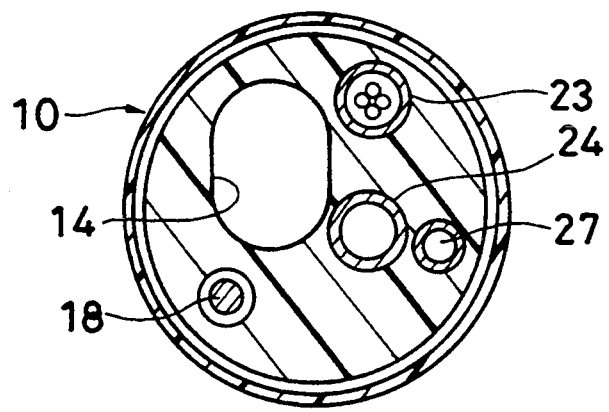
FIG. 3 is a sectional view of the end portion of the first embodiment shown in FIG. 1, taken along the line C—C.

FIGS. 1 to 3 show the structure of a first embodiment of a side-looking type electronic endoscope which allows a manipulating tool to be inserted thereinto according to the present invention. In FIG. 1, which is a sectional view of the end portion of the first embodiment disposed with a forceps insertion hole facing downward, an end portion 10 is connected to a curved portion 11 with wires 12A and 12B which are connected to an operating portion attached thereto. By operating these wires 12A and 12B, it is possible to bend the end portion 10. In the end portion 10, a forceps insertion hole 14 is formed in such a manner as to communicate with a manipulating tool insertion channel (forceps channel) 13 disposed in the curved portion 11 and to serve as the exit passage of the manipulating tool insertion channel 13. A manipulating tool 8 which is inserted into the endoscope through the manipulating tool insertion channel 13 is led out through the forceps insertion hole 14.

The forceps insertion hole 14 is so designed as to have an oval section having the major axis in the vertical direction, as shown in FIG. 3, so that the manipulating tool 8 inserted into the forceps insertion hole 14 can be bent with a large curvature radius from the manipulating tool insertion channel 13 toward the exit of the forceps insertion hole 14. The range of the endoscope in which the diseased portion can be treated largely depends upon the extent to which the manipulating tool 8 can be bent by a raising table 16. If the forceps insertion hole 14 as the exit passage is so designed as to have an oval section having the major axis in the direction in which the manipulating tool 8 is bent, thereby allowing the manipulating tool 8 to be bent at a large angle, as described above, the range of the endoscope in which the diseased portion can be treated is enlarged, thereby providing an endoscope having a good operability. Furthermore, in this embodiment, the lower wall of the forceps insertion hole 14 is a straight wall while the upper wall thereof is a curved wall, as indicated by the symbol R in FIG. 1, so that the manipulating tool 8 is bent with a larger radius of curvature.

As shown in FIGS. 1 to 3, the raising table 16 is supported by a shaft pin 17 so as to be rotatable towards the vicinity of the exit of the forceps insertion hole 14, and a wire 18 is connected to the raising table 16. By pulling the wire 18, it is possible to rotate the raising table 16 to a position indicated by a broken line 100. An arcuate groove 19 which is engaged with the manipulating tool 8 is formed in the raising table 16. When the manipulating tool 8 inserted into the forceps insertion hole 14 is raised by the raising table 16, the manipulating tool 8 maintains the rising state between the arcuate groove 19 and the inner wall of the forceps insertion hole 14, as represented by the broken line 8.

FIGS. 4 and 5 show the detailed structure of the raising table 16 of the first embodiment. The arcuate groove 19 has a radius which fits the curvature of the periphery of the manipulating tool 8 so as to be engaged with the manipulating tool 8, as shown in FIG. 5. The bottom line of the arcuate groove 19 is composed of a first arcuate portion 19A having a gentle curve, a second arcuate position 19B having a large curvature radius, a straight portion 19C, and an inverted arcuate portion 19D at the end of the raising table 16, as shown in FIG. 4. The curvature radius of the second arcuate portion 19B is coincident with the curvature radius of the bent portion of the manipulating tool 8 so that the second arcuate portion 19B comes into contact with the bent portion of the manipulating tool 8 when the manipulating tool 8 is raised by the raising table 16. By virtue of the arcuate portion 19B, not only is the force applied to the manipulating tool 8 dispersed, but also the direction of the force can be changed to the direction of the tangent of the arcuate portion 19B. The straight portion 19C is a portion with which the straight portion of the manipulating tool 8 at it end comes into contact. The manipulating tool 8 generally has a hard portion (straight portion) at its end, and a flexible portion is connected to the hard portion. In most cases, the hard portion of the manipulating tool 8 comes into contact with the straight portion 19C. The inverted arcuate portion 19D is provided in order to make the operation of unbending the bent portion of the manipulating tool 8 smooth when the raising table 16 is restored to the original position.

In FIG. 1, a CCD 20 is disposed slightly above the middle portion of the end portion 10, and an observation window 21 shown in FIG. 2 is optically connected to the CCD 20. An illumination window 22 is provided in the vicinity of the observation window 21. As shown in FIG. 3, an image guide 23 is connected to the observation window 21, and a light guide 24 is connected to the illumination window 22. As a result, the image of an object of observation obtained by projecting predetermined light thereon from the illumination window 22 is supplied to the CCD 20 through the observation window 21 and eventually displayed on a monitor. A nozzle 26 for jetting washing water therethrough is provided in the vicinity of the observation window 21, and an A(Air)/W (Water) supply passage 27 is connected to the nozzle 26, thereby enabling washing water or air to be supplied to the observation window 21 through the nozzle 26.

A supporting portion (not shown) having an operating portion through an inserting portion is integrally provided at the end portion 10 and the curved portion 11. In the supporting portion, a forceps introducing hole which communicates with the manipulating tool insertion channel 13 is provided, and a camera shutter button, knobs for vertical and horizontal angling and a knob for operating the raising table 16 through the wire 18 are provided in the operating portion.

According to the first embodiment of an electronic endoscope having the above-described structure, the manipulating tool 8 for executing various treatments while observing the photographed image of the object of observation through the observation window 21 is introduced from the forceps introducing hole to the forceps insertion hole 14 having an oval section through the manipulating tool insertion channel 13. At the point of time when the manipulating tool 8 projects from the forceps insertion hole. 14 by a predetermined length, if the wire 18 is pulled by turning the knob in the operating portion so as to raise the raising table 16, as shown in FIG. 6, the manipulating tool 8 is bent by using the curved wall R of the upper portion of the forceps insertion hole 14 having an oval section as a guide. When the raising table 16 is completely erect, the manipulating tool 8 is also guided along the arcuate groove 19, as shown in FIG. 6. In FIG. 6, a flexible portion 8B of the manipulating tool 8 comes into contact with the second arcuate portion 19b in a bent state, while a hard portion 8A comes into contact with the straight portion 19C. Accordingly, the manipulating tool 8 is guided by the second arcuate portion 19B and the straight portion 19C when the raising table 16 is erect. Especially at the second arcuate portion 19B, the force applied to the manipulating tool 8 for moving the manipulating tool 8 is dispersed, and the direction of the force can be changed to the direction of the tangent of the arcuate portion 19B, so that it is possible to introduce the manipulating tool 8 in the direction of the straight portion 19C smoothly in order to lead out the manipulating tool 8.

It goes without saying that the straight portion 19C stabilizes the manipulating tool 8 and prevents the force from being concentrated on only one portion. On the other hand, on the wall surface E at which the manipulating tool 8 comes into contact with the forceps insertion hole 14, the manipulating tool 8 is moved along the wall surface E in close contact therewith, so that contact resistance which obstructs the smooth movement of the manipulating tool 8 is not caused between the manipulating tool 8 and the wall surface E.

Figure 11:
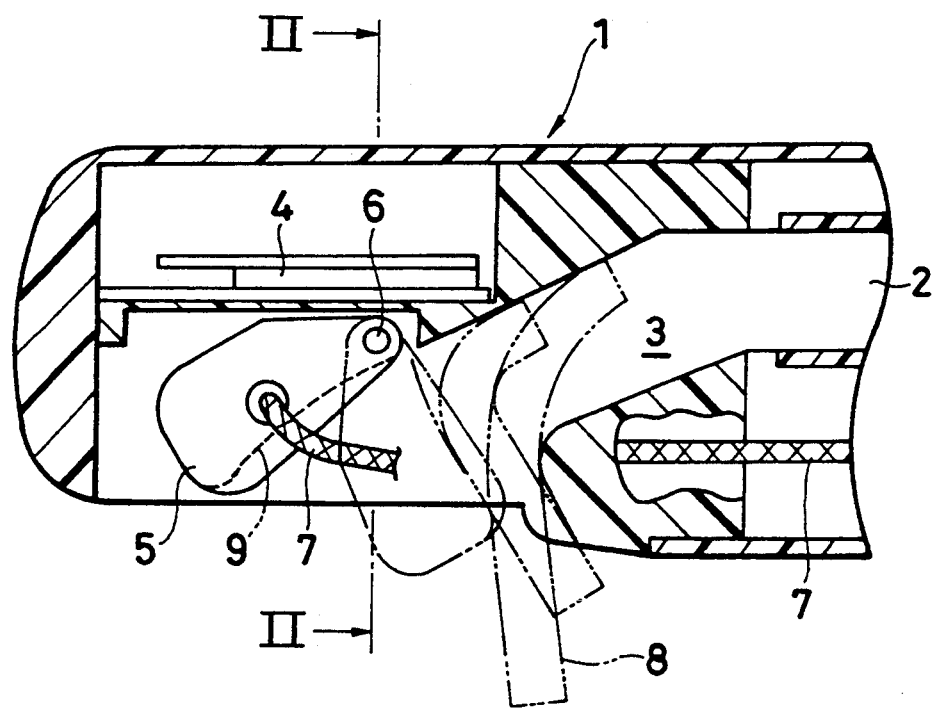
FIG. 11 is a sectional view of the structure of the side surface of the end portion of a conventional electronic endoscope.
Figure 12:
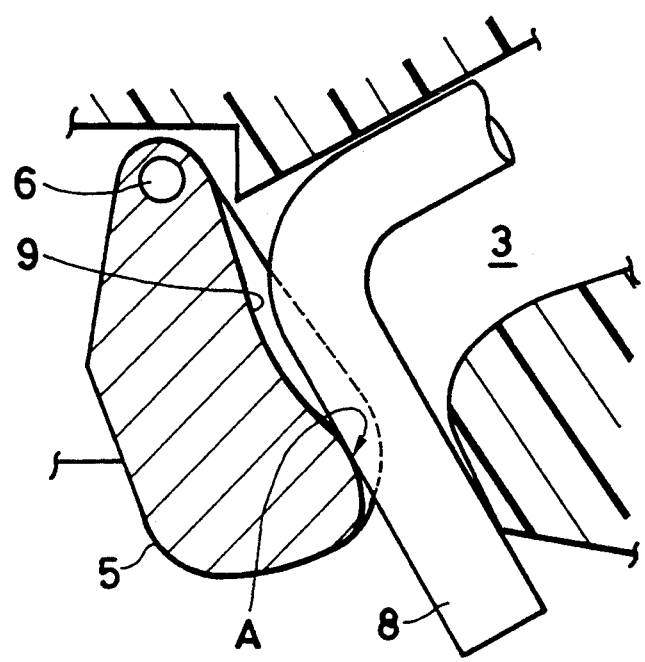
FIG. 12 is a sectional view of the conventional electronic endoscope shown in FIG. 11 in the state in which the manipulating tool is bent by the raising table.
Figure 13:
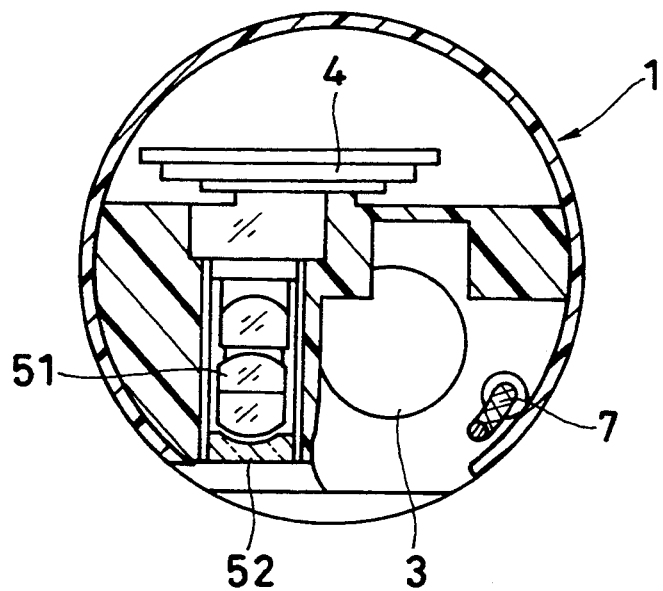
FIG. 13 is a sectional view of the end portion of the conventional electronic endoscope shown in FIG. 11, taken along the line B—B.

As described above, since the forceps insertion hole 14 as the exit passage has an oval section, the manipulating tool 8 is bent at a much larger angle than in a conventional endoscope, as will be obvious from comparison between FIG. 1 and FIG. 11. Since it is possible to bend the manipulating tool 8 with a large curvature radius, it is possible to relieve the manipulating tool 8 itself of unnecessary load. Although the forceps insertion hole 14 has an oval section in this embodiment, the same advantages are achieved by the forceps insertion hole having an elliptical section.

As described above, according to the first embodiment, when the raising table 16 is raised, it is possible to move the manipulating tool 8 smoothly while using the straight portion 19C as the guide and also to convert the force applied to the manipulating tool 8 to the force in the tangential direction of the arcuate portion 19B while dispersing the force by the arcuate groove 19B which guides the bent manipulating tool 8. In addition, since it is possible to reduce the load applied to the manipulating tool 8 itself due to the shape of the forceps insertion hole 14, it is possible to prolong the life of the manipulating tool 8 without impairing the function thereof.

Second Embodiment

Figure 7:
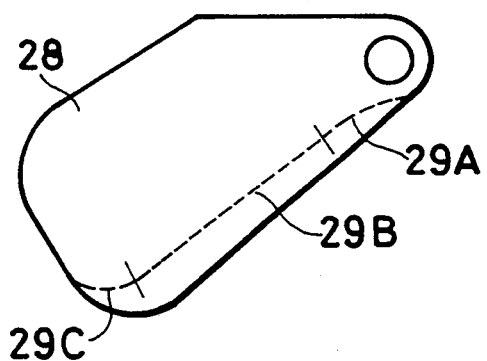
FIG. 7 is an elevational view of the structure of the raising table of a second embodiment of a side-looking type endoscope which allows a manipulating tool to be inserted thereinto according to the present invention.
Figure 8:
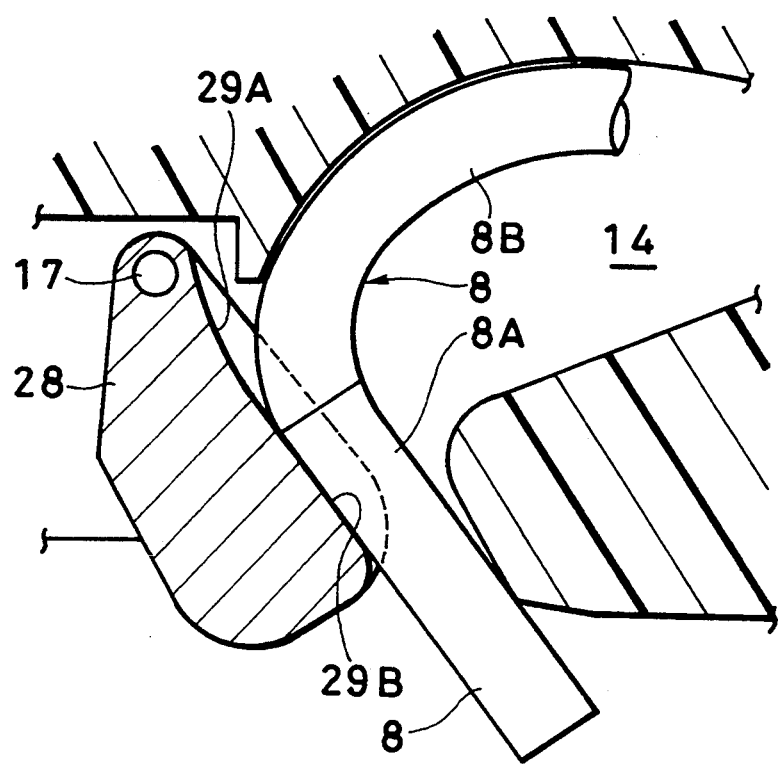
FIG. 8 is a sectional view of the second embodiment, in the state in which the manipulating tool is bent by the raising table.

FIGS. 7 and 8 show the structure of a second embodiment of the present invention. In this embodiment, the arcuate groove is mainly composed of a straight portion. As shown in FIG. 7, an arcuate groove 29 of a raising table 28 is composed of a gentle arcuate portion 29A, a straight portion 29B and an inverted arcuate portion 29C. In the second embodiment, it is impossible to convert the force applied to the manipulating tool 8 to the force in the tangential direction of the arcuate portion 19B unlike in the first embodiment. It is, however, possible to stabilize the manipulating tool 8 by the straight portion 29B and to utilize the force applied to the manipulating tool 8 as the leading force when the manipulating tool 8 is led out.

Third Embodiment

Figure 9:
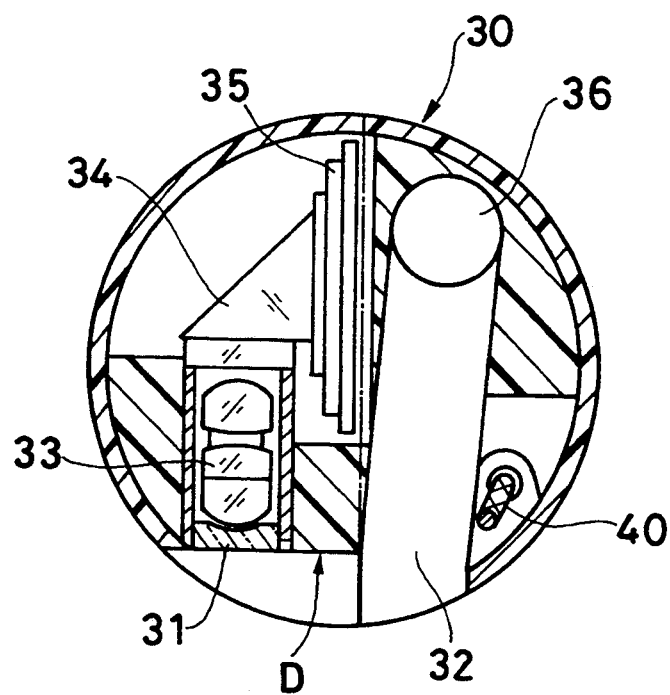
FIG. 9 is a sectional view of the front surface of the end portion of a third embodiment of a side-looking type endoscope which allows a manipulating tool to be inserted thereinto according to the present invention, taken at the observation window portion (left) and the forceps insertion hole portion (right)
Figure 10:
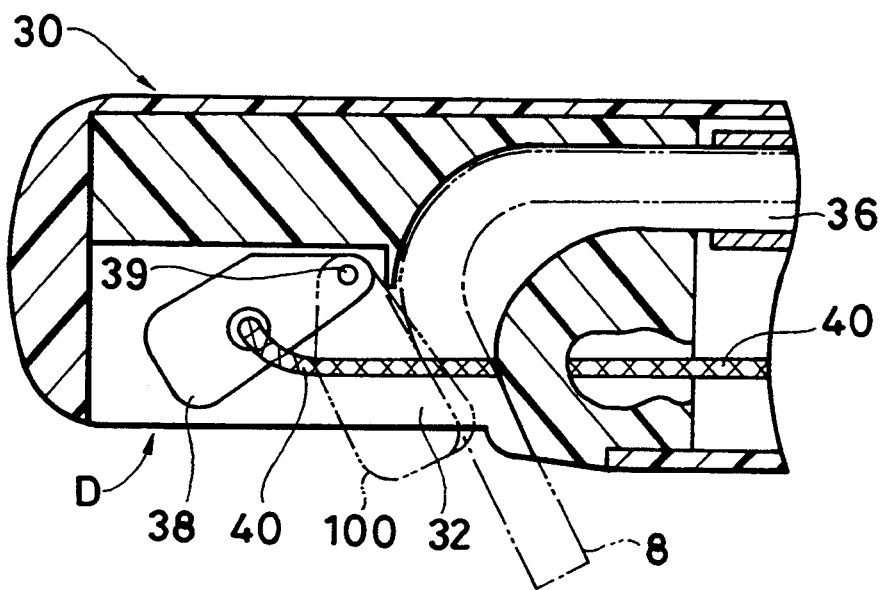
FIG. 10 is a sectional view of the side surface of the end portion of the third embodiment shown in FIG. 9.

FIGS. 9 and 10 show the structure of a third embodiment of the present invention. FIG. 9 is a sectional view of the main part of the end portion of an endoscope, taken at the observation window portion (left) and the forceps insertion hole portion (right), and FIG. 9 is a sectional view of the side surface of the end portion thereof. As shown in FIGS. 9 and 10, an observation window 31 is disposed in the lower portion of an end portion 30, and a forceps insertion hole 32 is provided so as to face downward. The under surface of the forceps insertion hole 32 constitutes the exit end surface D of the endoscope. An objective lens 33 is connected to the observation window 31, and a CCD 35, which is a solid-state image sensor, is connected to the objective lens 33 through a prism 34. In this embodiment, the forceps insertion hole 32 serves as the exit passage of a manipulating tool insertion channel 36, and the CCD 35 attached to the objective lens 33 through the prism 34 is disposed such that the surface of the device is perpendicular relative to the exit end surface D. Therefore, the optical axis of the observation window 31 and the objective lens 33 is bent by 90 degrees by the prism 34, and the image of the object of observation is formed in the image area of the CCD 35.

In this embodiment, since the CCD 35 is provided perpendicularly to the exit end surface D, the upper right portion in FIG. 9 remains vacant. Therefore, the manipulating tool insertion channel 36 is disposed as close to the upper surface of the end portion 30 as possible, and the forceps insertion hole 32 is curved at a large angle so as to communicate with the manipulating tool insertion channel 36 in a plane approximately parallel to the surface of the device of the CCD 35.

As shown in FIG. 10, a raising table 38 is supported by a shaft pin 39 so as to be rotatable towards the vicinity of the exit of the forceps insertion hole 32, and a wire 40 is connected to the raising table 38. By pulling the wire 40, it is possible to rotate the raising table 38 to a position represented by a broken line 100. It is therefore possible to raise the manipulating tool 8 lead out of the forceps insertion hole 32 to the position indicated by the broken line 8 by rotating the raising table 8.

According to the third embodiment of an electronic endoscope having the above-described structure, the manipulating tool 8 is introduced to the forceps insertion hole 32 as the exit passage through the manipulating tool insertion channel 36 while the image of the photographed object of observation is observed through the observation window 31. When the manipulating tool 8 projects from the forceps insertion hole 32, the knob is operated so as to raise the raising table 38 to the position indicated by the broken line 100. At this time, since the manipulating tool 8 is bent while being introduced through the greatly curved forceps insertion hole 32, the manipulating tool 8 is raised to the position indicated by a broken line. The manipulating tool 8 is bent at a much larger angle than in a conventional endoscope, as will be obvious from comparison between FIG. 10 and FIG. 11. Since it is possible to bend the manipulating tool 8 with a large curvature radius, it is possible to relieve the manipulating tool 8 itself of unnecessary load.

As described above, according to the third embodiment, it is possible to bend a manipulating tool 8 at a large angle by curving the exit passage at a large angle.

The structure of the third embodiment is applicable to an endoscope provided with a raising table having a similar structure to that in the first embodiment. It is also possible to apply the structure of the third embodiment to an endoscope provided with a forceps insertion hole having a similar structure to that in the first embodiment by appropriately modifying the design.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A side-looking endoscope which allows a manipulating tool to be inserted thereinto comprising:
   a manipulation tool insertion channel provided in said endoscope; and
   a raising table disposed in the vicinity of the exit passage of said manipulation tool insertion channel so as to bend a manipulation tool toward side surface of said endoscope in the state of being engaged with an arcuate groove which is formed in said raising table said arcuate groove comprising an arcuate portion with its bottom line bent so that the curved manipulating tool is guided at its stand position, and a straight portion with its bottom line linear on the end side of said raising table and situated so that the inclination of the straight bottom line is not aligned with and is different from a wall of the exit passage of the manipulating tool insertion channel when said manipulating tool straightened by means of the guide mechanism of said arcuate and straight portions comes into contact with the wall of the exit passage opposed to said arcuate groove.

2. A side-looking endoscope which allows a manipulating tool to be inserted thereinto comprising:
    a solid-state image sensor disposed at the end portion of said endoscope such that the surface of the device that is parallel to the image surface is perpendicular relative to the exit end surface of said endoscope;
    a manipulating tool insertion channel; and
    a raising table disposed in the vicinity of the exit of said manipulating tool insertion channel;
    wherein the exit passage of said manipulating tool insertion channel is bent in a plane approximately parallel to the surface of said device of said solid-state image sensor, 3. A side-looking endoscope which allows a manipulating tool to be inserted thereinto according to claim 2, wherein an arcuate groove is formed in said raising table in such a manner that said arcuate groove has a linear bottom line and the inclination of said linear bottom line when said raising table is erect is different from the inclination of the wall of the exit passage of said manipulation tool insertion channel which faces said arcuate groove.

4. A side-looking endoscope which allows a manipulating tool to be inserted thereinto according to claim 2, wherein an arcuate groove is formed in said raising table in such a manner that said arcuate groove has a linear bottom line and the inclination of said linear bottom line when said raising table is erect is different from the inclination of the wall of the exit passage of said manipulation tool insertion channel which faces said arcuate groove, and said exit passage of said manipulating tool insertion channel comprises an oval section with its longer diameter in the direction in which said manipulating tool is bent.

5. A side-looking endoscope which allows a manipulating tool to be inserted thereinto comprising:
    a manipulation tool insertion channel provided in said endoscope;
    a raising table disposed in the vicinity of the exit passage of said manipulation tool insertion channel so as to bend a manipulation tool toward a side surface of said endoscope in the state of being engaged with an arcuate groove which is formed in said raising table, said arcuate groove comprising an arcuate portion with its bottom line bent so that the curved manipulating tool is guided at its stand position, and a straight portion with its bottom line linear on the end side of said raising table and situated so that the inclination of the straight bottom line is not aligned with and is different from a wall of the exit passage of the manipulating tool insertion channel when said manipulating tool straightened by means of the guide mechanism of said arcuate and straight portions comes into contact with the wall of the exit passage opposed to said arcuate groove; and
    a solid-state image sensor disposed at the end portion of said endoscope such that the surface of the device that is parallel to the image surface is perpendicular relative to the exit end surface of said endoscope;
    wherein the exit passage of said manipulating tool insertion channel is bent in a plane approximately parallel to the surface of said device of said solid-state image sensor.

6. A side-looking endoscope which allows a manipulating tool to be inserted thereinto according to claim 1, wherein said exit passage has a curved wall line on the side where said raising table is disposed to permit guidance of said manipulating tool.

* * * * *